United States Patent [19]
Cremer

[11] Patent Number: 5,922,543
[45] Date of Patent: Jul. 13, 1999

[54] DETECTION AS CHROMOSOMAL TRANSLOCATIONS BY EXTENDING AND LIGATING DIFFERENTIALLY-LABELED PROBES HYBRIDIZED ON DIFFERENT SIDES OF A BREAK-POINT

[75] Inventor: Christoph Cremer, Heidelberg, Germany

[73] Assignee: Universitat Heidelberg, Heidelberg, Germany

[21] Appl. No.: 08/818,712

[22] Filed: Mar. 14, 1997

Related U.S. Application Data

[60] Provisional application No. 60/017,662, May 14, 1996.

[30] Foreign Application Priority Data

Mar. 15, 1996 [DE] Germany ............... 196 10 255.3

[51] Int. Cl.[6] ............... C12Q 1/68; C12P 19/34
[52] U.S. Cl. ............... 435/6; 435/91.1; 536/24.31
[58] Field of Search ............... 435/6, 91.1, 810; 536/24.31

[56] References Cited

U.S. PATENT DOCUMENTS

| | | | |
|---|---|---|---|
| 4,820,630 | 4/1989 | Taub | 435/5 |
| 5,057,410 | 10/1991 | Kawasaki et al. | 435/6 |
| 5,198,338 | 3/1993 | Croce | 435/6 |
| 5,424,413 | 6/1995 | Hogan et al. | 536/24.31 |
| 5,427,930 | 6/1995 | Birkenmeyer et al. | 435/91.52 |
| 5,529,925 | 6/1996 | Morris et al. | 435/252.3 |
| 5,567,586 | 10/1996 | Croce | 435/6 |

*Primary Examiner*—Kenneth R. Hoblick
*Attorney, Agent, or Firm*—Hardaway Law Firm, PA

[57] ABSTRACT

A composition and method of producing a composition which is directed to a single nucleic acid comprising a first section complementary to a sequence of a first chromosome, and comprising at least a first label, and a second nucleic acid section complementary to a sequence of a second chromosome, the second label being different from the first label. It is used for detecting translocations such that the single nucleic acid probe has different interactive labels on each side of a translocation break-point region.

11 Claims, 2 Drawing Sheets

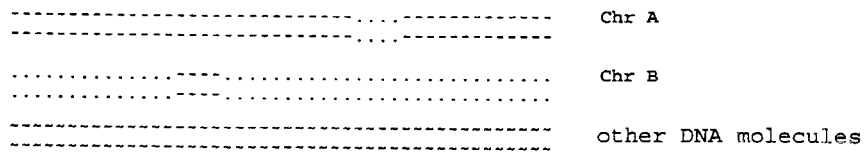

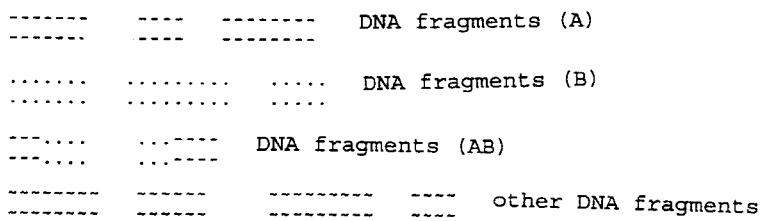

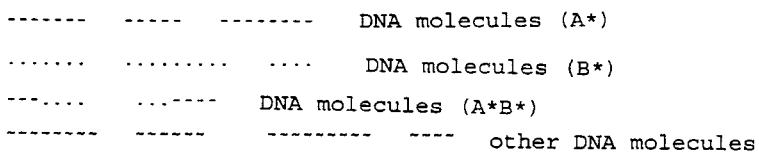

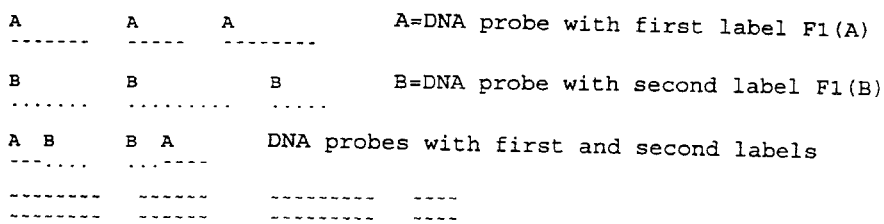

Figure 1A (isolated donor DNA)

```
----------------------------------------------  Chr A
----------------------------------------------

..............................................  Chr B
..............................................

----------------------------------------------  other DNA molecules
----------------------------------------------
```

Figure 1B (fragmentation)

```
-------    ----   --------    DNA fragments (A)
-------    ----   --------

.......    ........   .....   DNA fragments (B)
.......    ........   .....

---....    ...----           DNA fragments (AB)
---....    ...----

--------   ------  ---------  ----   other DNA fragments
--------   ------  ---------  ----
```

Figure 1C (denaturation)

```
-------    -----   --------   DNA molecules (A*)

.......    ........   ....    DNA molecules (B*)

---....    ...----            DNA molecules (A*B*)

--------   ------  ---------  ----   other DNA molecules
```

Figure 1D (hybridization)

```
A      A      A           A=DNA probe with first label F1(A)
-----  -----  --------

B      B      B           B=DNA probe with second label F1(B)
.....  ......  ......

A  B   B  A               DNA probes with first and second labels
---... ...---

-------- ------ --------- ----
-------- ------ --------- ----
```

Figure 1E (synthesis)

```
A------    A----    A-------
-------    -----    --------

B......    B........    B....
........   ..........   .....

A--B...    B..A---
---....    ..----
```

Figure 1F (isolation)

```
A------    A----    A-------     nucleic acid sequences with F1(A)

B......    B........  B....      nucleic acid sequences with F1(B)

A--B...    B..A--- nucleic acid sequences of the invention with F1(A)+F1(B)
```

Figure 1G (evaluation)

```
           B              B
AAAAAAAAAAAAAAAAAAAAAAAAAAAAA         occurrence of second labels F1(B)
|||||||||||||||||||||||||||||         in situ hybridization
-----------------------------         normal chromosome A
-----------------------------

A                   A
BBBBBBBBBBBBBBBBBBBBBBBBBBBBB         occurrence of first labels F1(A)
|||||||||||||||||||||||||||||         in situ hybridization
.............................         normal chromosome B
.............................
```

DETECTION AS CHROMOSOMAL TRANSLOCATIONS BY EXTENDING AND LIGATING DIFFERENTIALLY-LABELED PROBES HYBRIDIZED ON DIFFERENT SIDES OF A BREAK-POINT

This application claims the benefit of U.S. Provisional Application No. 60/017,662, filed May 14, 1996.

The present invention is relative to nucleic acids for demonstrating translocation breaking points or translocation positions on chromosomes and their method of production as well as a method for demonstrating translocation breaking points on chromosomes and translocations between chromosomes.

Exchanges of material between different chromosomes (translocations) are of great significance for various areas of medical research and diagnosis. For example, radiation-induced translocations can be used for the biological dosimetry of exposures to radiation which occurred a long time ago or are cumulative. In clinical diagnosis the determination of translocations and/or translocation breaking positions and translocation events on the corresponding chromosomes is essential because there is a close connection between the appearance of certain translocations and malignity (e.g. in leukemias).

In order to determine such translocation events three methods in particular are known in the state of the art:

(1) The analysis of metaphase cells of the persons to be examined with the aid of classic banding technology (F. Vogel, Human Genetics; Springer, Heidelberg (1992)).

(2) The analysis of cells in metaphase or of cell nuclei of the persons concerned by fluorescence in situ hybridization (FISH) with a FISH stain or with multi-stain FISH (T. Cremer et al., Human Genetics 80: 235 (1988); T. Cremer et al., Cytometry 11: 110 (1990); D. C. Tkachuk et al., Science 250: 559 (1990); S. Popp & T. Cremer, J. of Radiation Research Japan (Suppl.) 33: 61 (1992); C. Cremer et al., J. Radiation Research Japan (Suppl.) 33: 189 (1992); J. N. Lucas et al., Cytogenetics & Cell Genetics 62: 11 (1993)).

(3) The analysis of the DNA of cells of the persons concerned with the aid of polymerase chain reaction (PCR, "polymerase chain reaction") using starters for already identified breaking point regions (A. J. Fishleder et al., Leukemia 3: 746 (1989); C. R. Bartram et al., J. Exp. Med. 164: 1389 (1986); S. Hiroswa et al., Am. J. Hematol. 28: 133 (1988); M. S. Lee et al., Blood 73: 2165 (1989); E. S. Kawasaki et al., Proc. Natl. Acad. Sci. USA 85: 5698 (1988)).

The methods cited above can be used under suitable conditions—that is: (i) The cells of the donors can be removed under suitably protective conditions and cultivated for analysis or fixed onto microscope slides (cf. methods (1) and (2)) or (ii) The DNA analysis can be limited to a few breaking point regions (cf. methods (2) and (3)).

However, these conditions are frequently not met. For example, often only blood specimens are available in regions which have been clinically less developed which specimens do still permit the obtention of DNA but do not permit a satisfactory cell preparation. Furthermore, method 3 cited above using PCR for the analysis of isolated DNA is extremely expensive if a great number of possible breaking point regions of translocation events is being considered such as e.g. in the case of radiation-damaged cells or in the case of a tumor which has not yet been circumscribed more precisely with molecular biology.

The CGH ("comparative genomic hybridization") method known in the state of the art makes possible, starting from pure genomic DNA of a donor, the demonstration of any over- or under representations of DNA in comparison to the normal state as control given a minimum size of the sections to be detected of currently a few megabase pairs (mbp) length in at least 30% of the cells examined. However, the translocations and their breaking points, which are also extremely important clinically and scientifically, can not be demonstrated (A. Kallionemi et al., Science 258: 818 (1992); S. du Manoir et al., Hum. Genet. 90) 590 (1993); S. du Manoir et al., Cytometry 19: 27 (1995)).

Thus, the present invention has the problem of making available a novel system for demonstrating in particular frequently occurring translocations between chromosomes and translocation breaking points on chromosomes given the presence of isolated genomic DNA of a donor which system eliminates the above-mentioned disadvantages of the demonstration methods known in the state of the art.

This problem is solved by the embodiments of the present invention characterized in the claims.

In particular, a nucleic acid sequence specific for a translocation breaking point on a chromosome is made available comprising (1) A first sequence section which
  (i) Is complementary to a DNA sequence of a first chromosome,
  (ii) Is capable of hybridizing to this DNA sequence and
  (iii) Comprises at least a first label and (2) A second sequence section which
  (i) Is complementary to a DNA sequence of a second chromosome,
  (ii) Is capable of hybridizing to this DNA sequence and
  (iii) Comprises at least a second label with the first label and the second label being different.

BRIEF DESCRIPTION OF THE FIGURES

FIGS. 1A–1G are a schematic presentation of a preferred embodiment of the method of the invention for demonstrating translocation breaking points on chromosomes.

FIG. 1A shows genomic, double-stranded DNA molecules of a donor after isolation and optional amplification.

FIG. 1B shows double-stranded DNA-fragments of donor DNA after fragmentation on e.g. 1–2 kbp-long fragments, e.g. with the aid of restriction endonucleases.

FIG. 1C shows the DNA fragments of the donor DNA of FIG. 1B after denaturation.

FIG. 1D shows the hybridization using the denatured DNA fragments shown in FIG. 1C, also called single strands, as matrix, as well as shows DNA probes which stem from a first, normal chromosome (chr A) and carry a first label F1 (A), as well as DNA probes which stem from a second, normal chromosome (chr B) and carry a second label F1 (B).

FIG. 1E shows the synthesis of the nucleic acid sequence of the invention using the DNA probes from chr A and chr B hybridized to the individual strands (A*B)*); cf. step (e) of the method of the invention.

FIG. 1F shows the isolation of the nucleic acid sequence of the invention.

FIG. 1G shows the result of the evaluation of the in situ hybridization, carried out according to step (g), of the nucleic acid sequence obtained after isolation method I or II on normal, first chromosomes chr A and second, normal chromosomes chr B.

The concept "translocation breaking point" signifies molecular-genetically that position in the DNA sequence of a translocation chromosome at which sequences of a first chromosome are covalently connected to the sequences of a second chromosome; cytogenetically, "translocation breaking point" signifies that microscopically identifiable region containing this connection location. The concept "translocation event" signifies the new chromosomal configuration brought about by the exchange of material between a first chromosome and a second one (if necessary also further chromosomes).

The concept "nucleic acid sequence" signifies a semisynthetic, synthetic or modified nucleic acid molecule of deoxyribonucleotides and/or ribonucleotides and/or modified nucleotides such as e.g. a section from a known breaking point region obtained by oligonucleotide synthesis with fluorescence-labeled nucleotides, or a nucleic acid molecule synthesized by using a complementary nucleic acid as matrix using or co-using modified nucleotides.

The expression "sequence section capable of hybridization to a DNA sequence of a chromosome" signifies a specific sequence range of the nucleic acid sequence which is present as a single strand, is preferably 100 to 1000 base pairs long and which attaches itself, under formation of hydrogen bridges, to a complementary sequence of a chromosome at a suitable temperature, preferably at 70° or less, and at a suitable saline concentration containing preferably 50 to 300 mmol/l monovalent ions and 0–10 mmol/l bivalent ions.

The concept "label or labeling" signifies suitable atoms or molecules which can be demonstrated directly or indirectly and are inserted into the corresponding sequence sections of the nucleic acid sequence. Suitable labels are e.g. those comprising fluorescent dyes coupled to nucleotides and/or biotin and/or digoxigenin and/or nucleotides labeled with radioactive isotopes. In a preferred embodiment the first and the second labels are fluorescent dyes with a difference in the fluorescence behavior of the emission spectra sufficing for the detection of small amounts of substance, such as e.g. coumarines and rhodamines, and/or of the fluorescence lifetimes, such as e.g. fluoresceinisothiocyanates and europium chelate-labeled and/or porphyrin-labeled avidines.

The expression "sequence section with a label" signifies a covalently linked, linear sequence of nucleotides with one or several of the previously defined labels within the sequence section. For example, a 5'-terminally localized sequence section of the nucleic acid sequence can contain only one 5'-terminal label or all nucleotides of the sequence section or a part of them can be labeled.

The concepts "first sequence section" and "second sequence section" signify that the first sequence section, given suitable stringency conditions, is essentially not capable of hybridizing to the sequence complementary for the second sequence section in a second chromosome or to the sequence stemming from a second chromosome and complementary for the second sequence section in a first chromosome. This also applies, with the necessary changes, to the second sequence section, that is, the second sequence section essentially does not attach itself under suitable stringency conditions to the sequence complementary for the first sequence section in a first chromosome or to the sequence stemming from a first chromosome and complementary for the first sequence section in a second chromosome. The sequence sections can be localized within and/or terminally in the nucleic acid sequence of the invention. The sequence sections are connected directly, preferably via a 3',5'phosphodiester bond, or via a bond or a nucleic acid sequence which does not influence in a disadvantageous manner the above-defined hybridization of the first and of the second sequence section.

The concepts "first label" and "second label" signify that the first label differs so strongly in at least one parameter suitable for a demonstration, e.g. in a differing wavelength of the fluorescence, or in the fluorescence lifetime, or in the emitted fluorescence spectrum, that a detection of the first label is possible even given the presence of a large amount of the second label. If e.g. a traditional epifluorescence lens with a resolution of 150 nm is used in the detection, the result is that a detection of the first label must also be possible given the presence of an amount greater by up to four orders of magnitude, measured e.g. in the number of labeled nucleotides.

Further subject matter of the present invention is constituted by a method of producing the previously defined nucleic acid sequence, comprising the steps:

(a) Cleaving of genomic DNA comprising at least one translocation breaking point between two chromosomes into DNA fragments, (b) Denaturation of the DNA fragments into single strands, (c) Hybridization of the single strands in solution with a first batch of DNA probes which comprise a first label and are specific for a first chromosome, and with a second batch of DNA probes which comprise a second label and are specific for a second chromosome, in a reaction batch, (d) Synthesis of the nucleic acid sequence using the DNA probes hybridized onto the DNA fragments as starter in the presence of nucleotides and of at least one agent suitable for the synthesis of nucleic acids and of one agent suitable for linking nucleic acids, preferably via 3',5'-phosphodiester bonds, and (e) Isolation of the synthesized nucleic acid sequence from the reaction batch, especially from the DNA fragment used for its synthesis, in which the first sequence section of the nucleic acid sequence comprises a DNA probe from the first batch and the second sequence section of the nucleic acid sequence comprises a DNA probe from the second batch.

The concept "splitting of genomic DNA" signifies chemical and/or physical and/or enzymatic splitting of genomic DNA of a donor, e.g. from *homo sapiens sapiens*.

The genomic DNA can be obtained before step (a) by isolation from a suitable donor organism. The isolation of genomic DNA comprises the separation of the DNA from donor cells from the proteins of the donor cells. The genomic DNA can be isolated according to methods known in the state of the art from components containing nucleated cells such a blood specimens or tissue specimens of the donor (e.g. A. Kallionemi et al., Science 258: 818 (1992). There are also commercially available methods such as e.g. the Quiagen-DNA-Isolation Kit from DIAGEN. The genomic DNA of the donor can be amplified after the isolation in a suitable manner if necessary, e.g. with the aid of DOP ("degenerated oligo-primer-PCR")-PCR (H. Telenius et al., Genes, Chromosomes & Cancer 4: 257 (1992)). Alkaline compounds, the use of shearing forces or ultrasound, endonucleases or other nucleic-acid-splitting agents can be cited as examples for the splitting of genomic DNA. If only a slight amount of genomic DNA isolated directly from the donor is present the entire DNA can also be first amplified by PCR with degenerated primers according to known methods (H. Telenius et al., Genes, Chromosomes & Cancer 4: 257 (1992)).

The concept "denaturation" signifies the conversion of DNA present in double strands into single strands, e.g. by thermal treatment under suitable buffer conditions (J. Marmur & P. Doty, J. Mol. Biol. (1962) 5:109) and/or by denaturing chemical agents.

The concept "hybridization" or "attachment" signifies the formation of hydrogen bridges between complementary sequence sections of different nucleic acid molecules, especially between the DNA probes used in accordance with the invention and the DNA fragments at a suitable temperature, preferably at 70° C. or less and at a suitable saline concentration containing preferably 50 to 300 mmol/l monovalent ions and 0–10 mmol/l bivalent ions. The conditions are to be selected in such a manner that the total number of hydrogen bridges formed between complementary bases is sufficient to make a stable binding possible under the conditions of stringency selected.

The concept "batch of DNA probes" signifies DNA molecules which stem from a specific chromosome to be investigated, e.g. from a commercially available chromosome-specific DNA library of homo sapiens sapiens, which chromosome does not exhibit, as a "normal chromosome" any translocations. According to the above definition the DNA probes are capable of hybridization or attachment and are present in single strands in the reaction batch before the hybridization. Moreover, the DNA probes can comprise flanking sequences which make essentially no contribution to the attachment or hybridization. Moreover, chromosome-specific DNA libraries can also be obtained by laser-activated, flow-cytometric sorting or microdissection methods from specific chromosomes and subsequent amplification of the chromosomal DNA. Instead of chromosome-specific DNA libraries from homo sapiens sapiens, libraries of other species can also be used. For example, chromosome libraries of closely related species can also be used for the production of the nucleic acid sequence of the invention for investigations with human genomic donor DNA.

The concepts "first batch of DNA probes" and "second batch of DNA probes" signify that each of the two batches stems from a different chromosome of the genus of the donor, e.g. homo sapiens sapiens. For example, the first batch of DNA probes can stem from human chromosome 9 and the second batch of DNA probes from human chromosome 22, or the first batch of DNA probes stems from human chromosome 1 and the second batch of DNA probes stems from human chromosome 2. The batches of DNA probes can be obtained according to known methods (K. E. Davies et al., Nature 293: 374 (1981); C. R. Muller et al., Hum. Genet. 64: 110 (1983); C. Cremer at al., Cytometry 5: 572 (1984); J. C. Fuscoe et al., Cytogenet. Cell Genet. 43: 79 (1986); M. A. van Dilla et al., Biotechnology 4: 537 (1986); P. Lichter et al., Genet. Anal, Technol. Appl. 8: 24 (1991); B. Trask, Trends Genet. 7: 149 (1991)) or are commercially available (e.g. from Oncor or Vysis). According to the invention DNA from chromosomes of other species can also be used as batches of DNA probes. For example, it can be desirable for experimental animal, radiobiological or oncological studies to use chromosome-specific DNA libraries of the animal species investigated. It can also be advantageous for the production of a nucleic acid sequence in accordance with the invention for the examination of human donor DNA to use DNA from chromosomes of other species, especially closely related ones, as batches of DNA probes. In the latter instance the advantage of the method resides in a simplified elimination of ubiquitous repetitive sequences.

In an embodiment of the invention, instead of using two batches of DNA probes with a first and a second label, it is possible to use further batches of DNA probes with a third, fourth label etc. stemming from a third, fourth, etc. chromosome.

The concept "reaction batch" signifies a reaction mixture containing, in addition to the nucleotides and ATP, at least one agent suitable for synthesizing the nucleic acid sequence, at least one agent suitable for linking nucleic acids, at least one or several DNA probes from a first batch and one or several DNA probes from a second or further batch and one or several DNA fragments as matrices; further nucleic acids not participating in the method of the invention can also be present. The concentrations of the DNA probes and/or of the DNA fragments in the reaction batch are adjusted according to known methods (P. Lichter et al., Hum. Genet. 80: 224 (1988); B. Alberts et al., Molecular Biology of the Cell, 3rd edition, Garland Publ., New York & London (1994)).

The concept "synthesis of the nucleic acid sequence" comprises (i) the production of a "lengthening product" covalently bound to the 5'-terminal DNA probe, attached to the complementary sequence of a DNA fragment, from the first or second batch as starter via e.g. a phosphodiester-, thioester- or amide bond, and (ii) The linking of the lengthening product to a DNA probe, attached to the complementary sequence of the DNA fragment, of the corresponding other batch. The primary sequence of the resulting reaction product is complementary to the corresponding sequence of the DNA fragment as matrix molecule. Non-labeled and/or labeled nucleotides can be used as nucleotides in this reaction. The reaction product of this "synthesis" is thus the nucleic acid sequence of the invention containing at least one DNA probe from the first batch, one DNA probe from the second batch and one "synthesized" lengthening product located between these DNA probes. Before the isolation from the reaction mixture the nucleic acid sequence of the invention forms a double-stranded molecule with the corresponding complementary sequence of the DNA fragment used as matrix.

The concept "an agent suitable for synthesizing the nucleic acid sequence" signifies a native enzyme or a synthetically produced agent which acts as catalyst in the synthesis of the lengthening product in conjunction with suitable buffer conditions and other known compounds required for the reaction. Examples of native enzymes are the Taq polymerase, the Klenow fragment of DNA polymerase I, the E. coli DNA polymerase I and reverse transcriptase. Examples of "suitable buffer conditions" are the buffer conditions of PCR known in the state of the art. Examples of "other compounds" are salts like $MgCl_2$.

The concept "an agent suited for linking nucleic acids, preferably via 3',5'-phosphodiester compounds" signifies a native enzyme or a synthetically produced agent acting as catalyst in the linking of two molecules. Examples of native enzymes are DNA ligases such as T4-DNA ligase or E. coli ligase.

The concept "isolation of the nucleic acid sequence" signifies a method after the execution of which the nucleic acid sequence can be used for an in situ hybridization reaction on chromosomes or chromosomal DNA (also called "targets" in the following). Two isolation methods are explained in detail below.

Isolation Method I:

The nucleic acid sequence and the other double-stranded sequences contained in the reaction mixture are detached by thermal treatment under suitable buffer conditions and/or the addition of chemical denaturing agents from their matrix and/or from their complementary sequences and brought together with the likewise denatured targets and/or target sequences for the purpose of in situ hybridization under the optional addition of non-labeled repetitive DNA (e.g. human Cot I DNA) for the purpose of suppression according to known methods (P. Lichter et al., Hum. Genet. (1988) 80: 224; T. Cremer et al., Hum. Genet. (1988) 80: 235)). The addition of suppressing DNA can be omitted if the DNA sequences of a first and of a second chromosome used to produce the nucleic acid sequence do not contain repetitive sequences which would bind under the selected in situ hybridization conditions to complementary sequences of targets. Methods for the isolation and in situ hybridization of such DNA sequences are known (M. Schardin et al., Hum. Genet. (1985) 71: 281; D. Pinkel et al., Proc. Natl. Acad. Sci. USA (1986) 83: 2934; J. Wienberg et al., III. Plenary Workshop of the European Concerted Action "Automation in Molecular Cytogenetic Analyses", Ghent, 16 Nov. 18, 1995)).

Isolation Method II:

A separation of the nucleic acid sequence from the other sequences of the reaction mixture is performed in order to raise the in situ hybridization efficiency. Various methods can be used to this end:

(i) The labeling is carried out in such a manner that after denaturation of the double-stranded DNA sequences of the reaction mixture a separation of the doubly labeled nucleic acid sequence from the non-labeled sequences and from the singly labeled sequences is carried out by density gradient centrifugation.

(ii) The labeling is carried out in such a manner that the nucleic acid sequence is separated by methods of column chromatography.

In a first embodiment of point (ii) those DNA sequences are first bound with column chromatography which carry a first label. The separation of those DNA sequences which either carry no label or a second label takes place therewith. The bound DNA sequences carry either only a first label or a first and a second label. These DNA sequences are subsequently eluted and then subjected to a second separation by column chromatography in which the DNA sequences are bound in the case of which there is an affinity between column and second label. The separation of those DNA sequences carrying only a first label from those DNA sequences bound in the second step which have a first and a second label takes place therewith. The isolation of the nucleic acid sequence of the invention is concluded in accordance with the invention with the elution of the latter DNA sequences. According to the invention the isolated nucleic acid sequence can still be optionally amplified before the in situ hybridization with the aid of PCR methods (H. Telenius et al., Genes, Chromosomes & Cancer 4: 257 (1992)).

In another embodiment of point (ii) the first and the second labels are selected in such a manner that in addition to the optical properties selected in accordance with the invention, differences in the electrophoretic mobility occur. The separation then takes place with methods of two-dimensional gel electrophoresis known in the state of the art.

According to the invention isolation method II can be modified in such a manner that isolations of nucleic acid sequences are possible in the case of which first and second labels and third and fourth labels etc. occur. The isolation method can be modified e.g. in such a manner for this instance that all nucleic acids are bound in parallel or serially in a first column with a first label, in a second column all nucleic acids are bound with a second label, in a third column all nucleic acids are bound with a third label, and so forth. In a second method step columns are used in which the nucleic acids separated in the first step are used with a first label and of these all nucleic acids are bound which also contain a second label or also a third label, and so forth. In a further column the nucleic acids with a third, fourth, and so forth label are separated which were separated in the first method step on account of a second label, and so forth. On the whole, all techniques are in accordance with the method which result in a separation of nucleic acid sequences in accordance with the invention with a first and a second label, with a first and third label and so forth, with a second and third label, with a second and fourth label and so forth, from DNA molecules with only one type of label.

The individual method steps (a) to (e) are explained in detail in the following to the extent necessary.

In step (a) the optionally amplified genomic DNA with e.g. suitable restriction endonucleases is split into DNA fragments into sufficiently long, e.g. approximately 1–2 kbp, double-stranded DNA fragments in a suitable buffer solution, e.g. 1× SSC, PBS, etc. according to known methods (A. Kallionemi et al., Science 258: 818 (1992); S. du Manoir et al., Hum. Genet. 90: 590 (1993)).

In step (b) the solution of step (a) containing the DNA fragments is denatured, preferably without the addition of denaturing agents, e.g. by being heated to approximately 85–95° C. and after the denaturation the DNA fragments are present essentially in single strands.

In step (c) the solution of step (b) containing the single-stranded DNA fragments is subjected to a hybridization in solution. The added hybridization partners are e.g. labeled DNA probes approximately 100 to 300 bases long from at least two different batches, .e.g. from chromosome-specific DNA libraries of normal chromosomes. The "hybridization" or "attachment" takes place at a temperature which depends on the type of the nucleic acids present in the reaction batch. For example, the hybridization can take place at approximately 50 to 70° C. If translocation breaking points are present in the examined chromosomes of the donor, DNA fragments containing, among other things, translocation breaking points are present in the "hybridization solution" to which one or several DNA probes from a first batch of DNA probes and one or several DNA probes from a second batch of DNA probes have attached themselves, which attached DNA probes are differently labeled.

The hybridization of the invention can also be carried out with more than two batches of DNA probes. For example, a batch of DNA probes provided with a first label and from a chromosome-specific DNA library of a first chromosome, a batch of DNA probes provided with a second, third, fourth, and so forth label and from a chromosome-specific DNA library of a second, third, fourth, and so forth chromosome can be used simultaneously for the hybridization. In this instance DNA probes of differing labels attach themselves to DNA fragments of the chromosomes concerned which fragments contain translocation breaking points. For example, DNA fragments are present in the solution upon the presence of a translocation breaking point between a third and a fourth chromosome in which DNA fragments a nucleotide sequence of a third chromosome is linked to a nucleotide sequence of a fourth chromosome via covalent bonds. In the course of the hybridization reaction DNA probes of a third chromosome with a third label as well as DNA probes of a fourth chromosome with a fourth label attach themselves to these DNA fragments.

In an embodiment of the invention steps (a), (b) and (c) can be carried out in the same reaction container.

In step (d) the synthesis of the lengthening product is carried out at a temperature which depends in particular on the agent suitable for the synthesis, yielding reaction products in accordance with the definition cited above. For example, the synthesis takes place using the Taq polymerase at a temperature between approximately 70 to approximately 80° C., preferably 72° C., for approximately 1 to 15 minutes, preferably 5 minutes.

In particular, the gaps between the attached DNA probes of step (c) are closed with the aid of e.g. specific polymerases and the addition of nucleotides and ATP, during which a DNA strand which is covalently bound but comprises two different labels and is attached to the DNA fragment functioning as matrix is produced as reaction product.

The reaction batch has a suitable volume, e.g. 20 to 200 μl, and contains (1) a concentration of desired nucleotides suitable for the synthesis of the lengthening product, preferably 5 to 100 nmoles, more preferably approximately 20 nmoles, (2) units of a synthesizing agent sufficing for the synthesis of the lengthening product, e.g. 1 to 15 units, preferably 5 units Taq polymerase, (3) units of a suitable agent sufficing for the linking of the nucleic acids (e.g. a commercially available ligase) as well as DNA probes and DNA fragments in a suitable reaction solution using known method protocols (P. Leder et al., Science 196: 175 (1977); C. R. Muller et al., Hum. Genet. 64: 110 (1983). Aside from the cited compounds the reaction solution contains $MgCl_2$ (1 to 200 mmoles, preferably 1 to 50 mmoles, more preferably 1 to 20 mmoles and most preferably 3 mmoles), NaCl (30 to 300 mmoles, preferably 50 to 250 mmoles, more preferably 100 to 200 mmoles and most preferably 160 mmoles) and/or KCl (10 to 70 mmoles, preferably 30 to 70 mmoles, more preferably 40 to 60 mmoles and most preferably 50 mmoles) and or tris(hydroxymethyl)amino methane ("tris"; 5 to 50 mmoles, preferably 5 to 30 mmoles, more preferably 5 to 20 mmoles and most preferably 10 mmoles) and/or tween 20 (polyoxyethylene sorbitan monolaurate) (0.01 to 0.1% by volume, preferably 0.01 to 0.06% by volume, more preferably 0.01 to 0.04% by volume and most preferably 0.02% by volume) and optionally gelatine (0.1 to 1 mmole). The pH of the reaction solution is in a suitable range, especially one dependent on the synthesizing agent, preferably between 6 and 8.

In step (d) a part of the nucleotides in the reaction batch can optionally be labeled as a positive control of the synthesis. Suitable labels are e.g. nucleotides coupled with biotin, digoxigenin or fluorescent dyes (e.g. rhodamine dyes, coumarin dyes) These labels of the nucleotides used in the synthesis can differ from the labels of the sequence section. According to the invention the nucleotides in the reaction batch can also be used in their native form.

In step (e) the nucleic acid sequences of the invention contained in the reaction mixture are separated from the matrix molecules used for their synthesis and optionally also from the other sequences contained in the reaction mixture. This can be carried out in accordance with the above-described isolation method I or II. According to the invention a denaturation such as described in step (b) can also be carried out. In particular, an isolation of the nucleic acid sequence based on their double labels is advantageous for an in situ hybridization in accordance with the invention.

The nucleic acid sequence of the invention can also be chemically synthesized given knowledge of the primary sequence, e.g. by sequencing a nucleic acid sequence produced by the method cited above with methods known in the state of the art. For example, 1 kbp long, synthesized marker sequences from a first chromosome with an interval of approximately 2 Mbp from each other can be combined by methods of molecular biology in a statistical manner with 1 kbp long synthesized marker sequences from a second chromosome also with an interval of approximately 2 Mbp. The mixture obtained in this manner then contains a large or the greatest part of the cytogenetically demonstratable, possible translocation breaking points between the first chromosome and the second chromosome. Such synthetic nucleic acid sequences in accordance with the invention are of interest e.g. for in situ hybridizations according to the COMET ASSAY described below.

The nucleic acid sequence of the invention can be used in conjunction with in situ hybridization methods to demonstrate translocation breaking points on chromosomes. In particular, the nucleic acid sequence of the invention can be used to demonstrate radiation-induced or chemically induced translocation breaking points as well as translocation breaking points in cells of tumor tissues or in tumor cells occurring individually. Translocation breaking points are, among other things, a measure for translocations. For example, two batches of labeled DNA probes are used of which the first batch with a first label stems from a normal chromosome 9 and the second batch with a second label stems from a chromosome 22. When using DNA fragments from a donor with a translocation from 9 to 22 and from chromosome 22 to chromosome 9, as is typical in patients with chronic myeloid leukemia, when the method of the invention is carried out a nucleic acid sequence with a second label is detected on a normal chromosome 9 and a nucleic acid sequence with a first label is detected on a normal chromosome 22. This shows corresponding translocation breaking points in the chromosomes 9 and 22 of the donor.

The frequency of translocations increases with the applied dose of ionizing radiation (Awa et al., J. Radiat. Res. (Japan) 19: 126 (1978)). This results in the possibility of a dose estimate when the physical dose is not known. Translocations are also observed after the action of chemical compounds (G. A. Folle & G. Obe, Intern. J. Radiat. Biol. 68: 437 (1995)). Since certain translocations and translocation breaking points are closely correlated with the formation of malignant tumors (D. C. Tkachuk et al., Science 250: 559 (1990)), the analysis of translocations and of translocation breaking points is furthermore clinically and diagnostically highly significant in diagnosis, prognosis and monitoring the course of carcinogenesis.

In situ hybridization methods using DNA probes of a first (or several) chromosomes with a first label and a second (or further) DNA probe(s) with a second (or further) label(s) of a second (or further) chromosome(s) for the direct identification of translocations on chromosomes of cells after the action of ionizing radiation or of tumor cells are known (T. Cremer et al., Hum. Genet. 80: 235 (1988); T Cremer et al., Cytometry 11: 110 (1990); S. Popp et al., Kerntechnik 55: 204 (1990); Lucas et al., Intern. J. Radiat. Biol. 62: 53 (1992); C. Cremer et al., J. Radiat. Res. (Japan) 33 (Suppl.): 189 (1992); Lucas et al., Cytogenet. Cell Genet. 62: 11 (1993).

However, in contrast to the cited in situ hybridization methods the nucleic acid sequence of the invention permits the identification of translocation breaking points which are present in cells of the donor, e.g. after the action of radiation and/or chemical agents and/or due to the presence of tumors, by in situ hybridization on "normal" chromosomes and on "normal" DNA. This makes it possible to carry out a detection of translocations in accordance with the invention even in those instances in which only DNA material can be obtained, e.g in populations in catastrophe areas without the possibility of sufficient cell preparation.

Another application is relative to the use of isolated DNA from tumor tissue or tissues containing tumor cells in order to obtain the nucleic acid sequence of the invention. With the aid of the in situ hybridization of the nucleic acid sequence on normal chromosomes and on normal DNA the translocation breaking points of the selected first and second chromosomes (even other chromosomes, if necessary) can be identified which are present in the cells of the tissue examined. This is of considerable clinical significance for the diagnosis, prognosis and monitoring the course of therapy in tumor diseases. Furthermore, this method is considerably significant for a posteriori examinations of translocations in archive material of cells after the action of ionizing rays and/or chemical agents or in archive material from tissues containing tumor cells. This is of great interest e.g. for tumor research.

According to the invention the simultaneous demonstration of translocation breaking points in more than two chromosomes can be carried out by multi-color labeling. To this end DNA probes of a first chromosome with a first label, DNA probes of a second chromosome with a second label, DNA probes of a third chromosome with a third label, etc. are used. The labelings are to take place in such a manner that each label can be distinguished from all others. The synthesis of the nucleic acid sequences of the invention takes place in the manner described above, with the difference that more than two types of labeled DNA probes are present in the reaction mixture. When using DNA probes of a first to a fourth chromosome, for example, and translocation breaking points between the first and the second as well as between the third and the fourth chromosome, nucleic acid sequences are obtained with a first and a second label as well as with a third and a fourth label. Isolation method I can be carried out as described above. Isolation method II is to be modified appropriately. For example, in the first column-chromatographic separating step the sequences are bound with a first and a third label and in the second column-chromatographic separating step the sequences are bound with a second and a fourth label. After the separating process has taken place nucleic acid sequences of the invention are used for a subsequent in situ hybridization which have either a first and a second label or a third and a fourth label.

Further subject matter of the present invention is constituted by a kit for demonstrating translocations between chromosomes and for demonstrating translocation breaking points on chromosomes. The use of such a kit in accordance with the invention results in an in situ hybridization mixture containing at least the previously defined nucleic acid sequence in a suitable buffer.

Further subject matter of the present invention is constituted by a method for demonstrating translocations between chromosomes and for demonstrating translocation breaking points on chromosomes comprising the steps:

(a) The isolation of genomic DNA to be examined from suitable cellular material of a donor, preferably a mammal such as *homo sapiens sapiens,*

(b) The cleaving of the genomic DNA into double-stranded DNA fragments, (c) The denaturation of the double-stranded DNA fragments into single strands, (d) The hybridization of the single strands with a first batch of DNA probes which have a first label and are specific for a first chromosome and with a second batch of DNA probes which have a second label and are specific for a second chromosome in a reaction batch, (e) The synthesis of nucleic acids using the DNA fragments present as single strands as matrix and the DNA probes as starter in the presence of nucleotides and at least one agent suitable for the synthesis of nucleic acids and of an agent suitable for linking nucleic acids, preferably via 3',5'-phosphodiester bonds, producing reaction products present in double strands, (f) The denaturation of the reaction products present in double strands into single strands, after which denaturation single-stranded nucleic acids with the first label, single-stranded nucleic acids with the second label and, given the presence of a translocation between the DNA of the first chromosome and the DNA of the second chromosome in the cells of the donor to be analyzed, nucleic acid sequences in accordance with the invention are present in the reaction mixture, (g) The in situ hybridization of the single-stranded nucleic acid sequences present in the hybridization mixture and optionally enriched by further method steps, with a first and a second control chromosome without translocations, or with DNA separated by single-cell gel electrophoresis and (h) The evaluation of the in situ hybridization via the different labels of the nucleic acid sequences separated in step (f), preferably with methods of fluorescence lifetime microscopy or method of confocal laser scanning fluorescence microscopy or methods of fluorescence near-field microscopy.

The concept "in situ hybridization" signifies in a general sense the sequence-specific attachment, realized by hydrogen bridges, of DNA probes and/or RNA probes and/or DNA analogue probes to DNA targets or RNA targets or chromosomal targets in situ. DNA probes are deoxyribonucleic acids of a suitable length with a base sequence suitable for the in situ hybridization and with a label adequate for the demonstration selected. RNA probes are ribonucleic acids of a suitable length with a base sequence suitable for the in situ hybridization and with a label adequate for the demonstration selected. DNA analogue probes are linear molecules with a sequence of bases (e.g. adenine, thymine/uracil, guanine, cytosine) suitable for the in situ hybridization in which the covalent connection between the bases is structurally homomorphous with a deoxyribose- or ribose backbone and with a label adequate for the particular demonstration. A preferred embodiment of DNA analogue probes are PNA molecules in which the bases are connected to a backbone of N-(2-aminoethyl) glycine units (M. Egholm et al., Nature 365: 566 (1993)).

The concept "in situ" signifies that the hybridization reaction is carried out directly at the site of the target in the individual biological objects to be examined (e.g. cells, chromosomes) or in their immediate vicinity (in a range of up to approximately 300 $\mu$m). For example, an in situ hybridization is given if a probe is hybridized onto a chromosome in the metaphase or onto a chromosome section in the interphase (T. Cremer et al., Cold Spring Harb. Symp. Quant. Biol. 58: 777 (1993)). One also speaks of in situ hybridization if nucleic acids largely free of histones and non-histone proteins function outside of the chromosomes as target to the extent that there is still a direct spatial connection with the biological object to be examined (e.g. even normal cells, normal DNA).

The concept "evaluation" signifies the optical demonstration of the nucleic acid sequence of the invention on normal first and/or second chromosomes (control chromosomes) A and/or B or on normal DNA from A and/or B separated by single-cell gel electrophoresis (also designated as "COMET ASSAY") after in situ hybridization. If e.g. a reciprocal translocation (mutual exchange of chromosomal material)

between A and B is present in the donor the targets are detected at the sites corresponding to the particular translocation breaking points upon analysis of a sufficient number of chromosome/DNA strands in situ by the nucleic acid sequence of the invention. The demonstration preferably takes place with methods of digital microscopy. In a preferred embodiment methods of fluorescence lifetime microscopy or confocal laser scanning fluorescence microscopy or of optical fluorescence near-field microscopy or a combination of these methods are used. When using further nucleic acid sequences with third, fourth labels etc. the concept "evaluation" signifies the identification and localization of the further nucleic acid sequences on the control chromosomes and the DNA strands in the COMET ASSAY. The identification takes place due to a differing label, e.g. a differing fluorescence time and/or a differing fluorescence spectrum and/or one or several differing fluorescence lifetimes or a combination of these methods.

The individual method steps are explained further in the following.

In step (a) genomic DNA from suitable cellular material of a donor, preferably of a mammal such as a human being or e.g. also of a mouse, rat, Chinese hamster is isolated according to methods known in the state of the art; see also preceding remarks concerning the concept "isolation of genomic DNA". For example, in a patient suspected of having a blood tumor which has not yet been limited more precisely a blood sample is taken and the genomic DNA isolated and amplified if necessary.

For steps (b) to (e) refer to the previously cited method, especially to the comments regarding steps (a) to (d) and its preferred embodiments for producing the nucleic acid sequence of the invention.

Regarding step (d) of the method of the invention note that the first and second chromosomes are any two normal chromosomes of the genome of the species of the donor. Moreover, according to the invention DNA probes of third, fourth or further chromosomes with a third, fourth or further labels can also be used.

Regarding step (f) of the method of the invention note that the denaturation of the reaction products present in double strands into single strands can be carried out based on the comments to step (b) of the previously cited method and its preferred embodiments for producing the nucleic acid sequence of the invention. When using third, fourth and further DNA probes comprising distinguishable labels there are additionally nucleic acid sequences of the invention with third, fourth and further labels.

In particular, in step (f) as preparation for carrying out step (g) e.g. in the previously described isolation method I the reaction products present in double strands in the reaction mixture are converted into single-stranded nucleic acid molecules according to methods known in the state of the art such as heat denaturation or pH-dependent denaturation with HCl or NaOH. Preferably, a denaturation without denaturing agents is carried out. For example, the separating of the reaction products into single strands can be achieved by heating the reaction mixture to approximately 90 to 100° C., preferably 95° C., for about 1 to 15 minutes, preferably 5 minutes.

In another embodiment it can be necessary after concluding e.g. isolation method II for carrying out step (g) to perform a denaturation of the enriched nucleic acid sequences as described above.

In step (g) an in situ hybridization is carried out on normal first and/or second chromosomes or on normal DNA from first and/or second chromosomes. Given the presence of a translocation between DNA of a first and DNA of a second chromosome in the cells of the donor to be analyzed, the in situ hybridization mixture contains at least the single-stranded nucleic acid sequence of the invention in a buffer suitable for the in situ hybridization.

In COMET ASSAY the in situ hybridization takes place on DNA fragments from donor DNA separated electrophoretically in situ or on control DNA, separated electrophoretically in situ, from cells without translocation breaking points between the chromosomes concerned.

In the additional use of nucleic acid sequences with third, fourth and further labels the in situ hybridization takes place additionally with third, fourth and further control chromosomes or with DNA fragments separated in situ.

The control chromosomes can be located in metaphase preparations obtained from dividing cells of the donor species according to known methods. Another method in accordance with the invention consists in the using of control chromosomes placed onto slides after flow-cytometric sorting of isolated chromosomes. The placing takes place in such a manner that the control chromosomes of the various types are spatially separated from each other. According to the invention the chromosomes can be additionally labeled for a better localization of the nucleic acid sequences, e.g. with DNA stains without sequence specificity or by in situ hybridization with control DNA probes carrying a label not used in the synthesis of the nucleic acid sequence. For example, it is useful to label the centromere region as well as the telomere regions of the long and the short chromosome arm differently.

When using isolation method I previously described for the nucleic acid sequence the in situ hybridization mixture contains in addition to the nucleic acid sequence of the invention still other nucleic acids. In the case of two labels these are in particular the non-labeled DNA fragments, labeled DNA probes of a first and of a second chromosome as well as further simply labeled nucleic acids present in the reaction mixture step (f) as the result of the reaction process of DNA probes and DNA fragments. In this instance the concentration of the nucleic acid sequence of the invention in the in situ hybridization mixture is considerably lower than the total concentration of the other nucleic acid sequences cited here.

When using the previously described isolation method II for the nucleic acid sequence the latter is present in a concentration which is very enriched in comparison to isolation method I.

Numerous protocols are known for the general reaction conditions of an in situ hybridization. A few examples for carrying out the in situ hybridization reaction are cited in the following:

In situ hybridization example 1 (cf. D. Pinkel et al., Proc. Natl. Acad. Sci. USA 85: 9138 (1988); P. Lichter and T. Cremer, Human Cytogenetics, D. E. Rooney and B. H. Czepulkowski, eds., IRL Press Oxford, pp. 157ff (1992); C. Lengauer et al., Cancer Res. 52: 2590 (1992); A Hagemeijer et al., Genes, Chromosomes & Cancer 8: 237 (1993); P. M Kroisel et al., Cytogenet. Cell Genet. 65: 97 (1994); H. Yokota et al., J. Cell Biology 130: 1239 (1995)):

Chromosome preparations after methanol/glacial acetic acid fixation on glass slides or slide cover glasses are pretreated with RNase A and pepsin, re-fixed for 10 min in 3% paraformaldehyde and preserved in 70% ethanol. For the in situ hybridization reaction a 10 $\mu$l to 30 $\mu$l hybridization mixture of 25–50 ng or 100–150 ng of the fluorescence-labeled nucleic acid sequence of the invention is used in the presence of 3 to 5 $\mu$g or 10 $\mu$g or 30 to 100 $\mu$g unlabeled, commercially available Cot1 DNA in 50% formamide, 10% dextrane sulfate in 1× SSC or 2× SSC. 1× SSC is an aqueous solution of 150 mM NaCl and 15 mM sodium citrate. The hybridization mixture is left standing after a treatment of 2 to 5 minutes at 70° C. for the denaturation of the DNA for 1–3 hours at 37° C. for the "preannealing". The chromosome preparations are treated for 2 to 5 minutes at 65–75° C. in a denaturation mixture of 50–70% deionized formamide in 1× to 2× SSC, pH 7–75 and subsequently dehydrated with an alcohol series of 70%, 90% and 100% ethanol at 0 to 10° C. and air-dried. The in situ hybridization reaction takes place subsequently by means of the combination of the chromosome preparation with the hybridization mixture after the end of the "preannealing" at approximately 37 to 42° C. for approximately 12 to 96 hours. Washing steps, e.g. three times 10 minutes each in 50% formamide, 2× SSC and 0.5% Tween 20 at 44° C. then take place, followed by 5 minutes washes in each of 4× SSC, 0.05% Tween 20 at 44° C. as well as at room temperature.

In situ hybridization example 2 (cf. DE-A-47 69 546; D. Celeda et al., Cytometry 17: 13 (1994); F. Haar et al., Biotechniques 17: 346 (1994); M. Durm et al., Exp. Techn. Physics, in press; M. Durm et al., Zeitschrift fur Naturforsch., in press; M. Durm et al., submitted for public.)):

Traditional chromosome preparations are used after methanol/glacial acetic acid fixation 3:1. The 10 to 30 μl hybridization mixture contains 10–50 ng of the nucleic acid sequence of the invention in 10 mmol/l tris-HCl, 3 mmol/l $MgCl_2$, 50 mmol/l KCl, 1 mg/l gelatine, 2× SSC in deionized water (pH 7–8). The hybridization mixture is placed at 15 to 25° C. onto the chromosome preparation located on a slide, covered with a slide cover glass and the cover glass sealed with a rubber material. The preparation containing chromosome preparation and hybridization mixture obtained in this manner is heated in a water bath for 5 minutes to approximately 85–95° C.; alternatively or additionally, electromagnetic microwave radiation can also be used. The preparation is subsequently cooled off in a suitable manner to temperatures above 55° C. but below 77° C. for approximately 15 to 150 minutes. After the hybridization reaction the cover glass is removed and the hybridized chromosome preparation treated for 5 minutes at room temperature with a washing buffer of 1× SSC or with 1× PBS (phosphate-buffered saline): 0.2 g/l KCl, 0.2 g/l $KH_2PO_4$, 8 g/l NaCl, 2.16 g/l $Na_2HPO_4 \times 7H_2O$; pH 7) and 0.2% Tween 20 or washed for 5 minutes in a solution of 0.9% NaCl and 0.2% Tween.

In situ hybridization example 3 (cf. M. Durm et al., Exp. Technique of Physics, in press; M. Kraus et al., Exp. Technique of Physics, in press):

This low-temperature method is only suited for certain nucleic acids in accordance with the invention, especially for those which can be performed with double-stranded DNA.

Chromosome preparations fixed according to standard methods are washed after a treatment with methanol/glacial acetic acid 3:1 with 100% ethanol and air-dried. The hybridization mixture (see in situ hybridization example 2) is heated for 5 minutes at 94° C. or for 10 minutes at 84° C. The chromosome preparation is heated to temperatures between approximately 37 and 52° C. The hybridization mixture (pH 7–7.5) is added after cooling off to ≦52° C. (see in situ hybridization example 2). The hybridization reaction of the preparation consisting of chromosome preparation and hybridization mixture is also carried out at temperatures between approximately 37 and 52° C. The washing procedure takes place according to in situ hybridization example 2.

In a preferred embodiment of the method of the invention the simply labeled nucleic acids present in the reaction mixture and, given the presence of a translocation, doubly labeled nucleic acid sequences are labeled with fluorescence stains and a fluorescence in situ hybridization (FISH) is carried out therewith.

The above-named in situ hybridization examples are intended solely to furnish information about the ability of the method to be carried out, given the plurality of the known possibilities, and are in no way to be considered as limiting the present invention. The FISH technique used in them is preferably carried out without using denaturing agents (see in situ hybridization examples 2, 3). However, traditional FISH methods can also be used (see in situ hybridization example 1).

Normal metaphase chromosomes from normal cells (metaphase preparations) or normal metaphase chromosomes from normal cells after enrichment by fluorescence-activated sorting can be used as targets for such "multi-color in situ hybridizations". The in situ hybridization of the invention can be formally described by the stringency of the in situ hybridization reaction. The concept "stringency" comprises here the extent of the complementary pairing of the nucleic acid sequence or of a cohesive part of it with the DNA of the chromosomal target or of the target DNA in the COMET ASSAY. A stringency of e.g. 90% signifies that of 100 successive bases on the nucleic acid sequence 90 are paired in a complementary manner. The stringency can be altered in its chronological course by the kinetics of the in situ hybridization reaction. The parameters of the reaction are to be selected in such a manner that after the hybridization time t the time-dependent stringency $S(t)$ results in the in situ hybridization labeling in accordance with the invention.

The stringency $S(t)$ of the in situ hybridization can be varied e.g. by the concentration of the amount of denaturing agents added. In the case of in situ hybridization methods without denaturing agents the stringency can be varied in particular by changing the parameters (i) hybridization temperature and (ii) hybridization time. Further parameters are e.g. the ion strength of the hybridization mixture, the degree of condensation of the targets, the length of the DNA probes as well as their labeling type. In the case of in situ hybridization on control chromosomes the stringency of the in situ hybridization is regulated in such a manner that a complementary pairing of a cohesive part of the base sequence of the nucleic acid sequence is sufficient for the bonding. For example, the stringency can be selected in such a manner that the binding of 300–500 successive bases of the nucleic acid sequence suffices.

In the case of in situ hybridization on electrophoretically separated DNA targets in the COMET ASSAY the stringency is selected to be so high that a stable binding of the nucleic acid sequence of the invention isolated e.g. according to isolation method II only occurs if the nucleic acid sequence hybridizes in its entire length with high complementarity.

Aside from chromosomal targets the DNA of individual cells prepared with the aid of COMET ASSAY or related methods is also viewed as a further target in accordance with the invention for the in situ hybridization. In COMET ASSAY (O. Östling and K. J. Johanson, Biochem. Biophys. Res. Commun. 123: 291 (1984); P. L. Olive and J. P. Banath, Exp. Cell Res. 221: 19 (1995)) cells are plated out after embedding into liquid agarose on a carrier and lysed in situ after formation of an agarose gel. The DNA of the individual cells is then separated in situ in an electric field. The smaller the fragment length is, the greater the amount of migration-capable DNA. Nucleic acid sequences obtained e.g. according to isolation method II are used for the in situ hybridization of the nucleic acid sequences of the invention to the electrophoretically separated DNA targets after carrying out of the COMET ASSAY preparation. The denaturation of the DNA target and the in situ hybridization reaction can not take place here at high temperatures without further measures (see in situ hybridization examples 1 and 2 for FISH technique), since agarose gel otherwise melts and the cells as well as the electrophoretically separated DNA targets can be washed away. One solution which can be carried out consists in carrying out the denaturation of the DNA target below approximately 40 to 45° C. with the aid of chemical agents, e.g. 0.1 mol/l HCl or 1 mol/l NaOH. The denaturation of the nucleic acid sequence of the invention takes place separately; see in situ hybridization examples 1 and 2 for the FISH technique. The stringency of the in situ hybridization conditions is selected in such a manner that only those nucleic acid sequences bind to the DNA target which have entered a complementary pairing with the preponderant majority of their bases. In this instance a detection of a doubly labeled nucleic acid sequence in the DNA of the cells after the COMET ASSAY indicates a translocation breaking point. This translocation breaking point is identical to a translocation breaking point in the cells from which the genomic DNA fragments used for the synthesis of the nucleic acid sequence were isolated.

For example, nucleic acid sequences in accordance with the invention are isolated using DNA from tumor tissue T1. After the COMET ASSAY cells are isolated from a tumor tissue T2 and used as target for the in situ hybridization as described above. A binding of the nucleic acid sequence detectable by its label shows the presence of the specific translocation from T1 in T2 too. This is quite interesting, even clinically, for a comparative characterization of tumor tissue. An example of an application would be the control of therapeutic measures. For example, the sequence of the invention can be isolated according to e.g. isolation method II from DNA from tumor tissue of a patient before the start of treatment as well as at various times during the therapy. The advantage of the COMET ASSAY is that no chromosomal preparations are required here. The renunciation of chromosomal assignment associated therewith can be accepted in certain instances.

In step (h) the in situ hybridization is evaluated. For example, in an in situ hybridization on chromosomes in metaphase preparations using nucleic acid sequences obtained e.g. according to isolation method I in a first evaluation step the chromosomes are identified which predominantly carry a first label, a second label, etc. When using sorted control chromosomes this evaluation step can be eliminated since the chromosomes were already identified on account of the sorting process. In this instance or when using control chromosomes identified in another way it is advantageous to use nucleic acid sequences obtained according to isolation method II. In a second step the locations of the nucleic acid sequences of the invention on the control chromosomes are detected. The identification of a nucleic acid sequence on a first control chromosome takes place e.g. based on its second label, if necessary also on further labels which can be distinguished from the first label. The identification of a nucleic acid sequence on a second control chromosome takes place e.g. based on its first label, optionally also on further labels which can be distinguished from the second label, etc. The determination of the site of the nucleic acid sequences on the control chromosomes takes place by indicating their relative position on the long or the short arm in relation to centromere, telomeres, as well as, if necessary, of further control labels.

Since in the hybridization of the invention, each nucleic acid sequence has only one binding site per individual chromosome, as a rule several, if necessary also many chromosomes must be evaluated in order to reach a reliable result about the presence and location of a translocation breaking point. For example, in the case of isolation method I for the nucleic acid sequence still further nucleic acid molecules are present in the hybridization mixture which compete with the nucleic acid sequence for the same binding site on the control chromosomes. In the case of the binding site on a first control chromosome these further nucleic acid molecules are e.g.: (i) The DNA probe with a first label and (ii) The non-labeled DNA fragment complementary with the binding site. How frequently a binding of the nucleic acid sequence to the binding site can occur depends on its relative frequency in the hybridization mixture. When using isolation method II this relative frequency can be considerably increased and the number of chromosomes to be evaluated considerably reduced therewith. The evaluation can be supported by methods of automatic digital image analysis, which make possible an identification of chromosomes as well as of individual hybridization sites (P. Emmerich et al., Exp. Cell Res. 181: 126: (1989); S. Popp et al., Kerntechnik 55: 204 (1990); C. Cremer et al., J. Radiat. Res. (Japan), Suppl., 33: 189 (1992); J. A. Fantes et al., Int. J. Radiat. Biol. 68: 263 (1995)).

There are known methods for evaluation in the state of the art, e.g. on a cytochemical basis, or time-resolved microscopic fluorescence methods (L. Seveus et al., Cytometry 13: 329 (1992); T. Gadella et al., Biophys. Chemistry 48: 221 (1993)). These methods permit the autofluorescence of a biological object and the fluorescence of another stain with fluorescence emission of the same wavelength to be separated from the fluorescence of the hybridization signal. A prerequisite for this is a sufficient difference in the fluorescence decay times. For example, the fluorescence decay time of autofluorescence is 100 nanoseconds and less. The decay times of fluorescein and rhodamines is less than 10 nanoseconds. On the other hand, the fluorescence decay times of lanthanide chelate compounds are 10 to 1000 microseconds. Such fluorochromes with very different decay times can be coupled directly or indirectly to DNA probes. For example, a europium compound can be detected at an excess of another fluorochrome with very different decay time still at an excess of $1 \times 10^6$. A normal metaphase chromosome, e.g. the human X chromosome, consists of approximately 160 million base pairs which take up a volume of approximately 10 $\mu m^3$ in a chromosome preparation. The volume of the metaphase chromosome detected in a traditional fluorescence microscope based on the resolution is approximately 1 $\mu m^3$, in which approximately 16 million base pairs with autofluorescence or a different label with a very different decay time are present. If one starts e.g. with a nucleic acid sequence in accordance with the invention of 200 to 500 base pairs to be detected, the excess of DNA stained in another way in the volume to be analyzed is approximately $3 \times 10^4$ times up to $8 \times 10^4$ times, that is, more than one magnitude less than the tolerable excess of $1 \times 10^6$ times. The detection volume and therewith the excess to be tolerated can be limited still further to a considerable extent by confocal laser scanning fluorescence methods. This example is intended solely to show the ability of the detection method to be carried out. Alternative detection methods are also within the protective scope of the present invention in as far as they result in a demonstration of the nucleic acid sequence on metaphase chromosomes and in COMET ASSAY preparations.

Detection methods used in accordance with the invention are characterized in that they permit a demonstration of fluorescence-labeled DNA strands of a few hundred bases and less in fluorescence in situ hybridization methods (FISH).

For example, the nucleic acids hybridized to a first chromosome and simply labeled with fluorescent stains and, given the presence of a translocation, the hybridized nucleic acid sequences double-labeled with fluorescent stains can be subjected to a highly sensitive fluorescence detection, as described above. The non-hybridized part of the double-labeled nucleic acid sequence is complementary hereby, under suitable stringency conditions and given the presence of a translocation, to a section on a second chromosome; that is, the double-labeled nucleic acid sequence bound to the chromosomal target represents the breaking point region. It should be noted in this connection that an attachment of a molecule complementary only in a cohesive partial section can be achieved even in the case of high stringency. This results from the known fact that in situ hybridizations with phage DNA containing the complementary human DNA section inserts can be realized on human chromosomal targets with high stringency of the hybridization of the insert.

When using rather high stringency conditions it can be achieved when using the COMET ASSAY that a double-labeled nucleic acid sequence obtained according to isolation method II binds with the preponderant majority of its bases over its entire length to the DNA target. Nucleic acid molecules of the donor are labeled in this manner which contain a corresponding translocation breaking point.

The site of the mixed-stained and double-labeled molecules on the normal chromosomes is then detected with highly sensitive detection methods. The equipment required for this can be selected in various designs. A few exemplary embodiments are indicated in the following.

Evaluation Example 1 (L. Seveus et al., Cytometry 13: 329 (1992)):

A traditional epifluorescence microscope is used which is set up for time-resolved fluorescence detection. When labeling the nucleic acid sequence of the invention is labeled with long-lived fluorochromes in the range of a few hundred microseconds, e.g. a pulsed xenon flash lamp is used for excitement. A rotating chopper plate is located in the ray path of the fluorescence emission. This allows the fluorescent light to be detected with a certain time delay after the excitement pulse. A cooled CCD (charged coupled device) camera can be used for detection.

Evaluation Example 2 (T. Gadella et al., Biophys. Chemistry 48: 221 (1993)):

A continuous laser excitation source in conjunction with a traditional epifluorescence microscope is used which is modulated with a high frequency, e.g. 25–80 MHz. The lifetime of the modulated fluorescence emission can be determined from the phase delay and the modulation depth of the fluorescent signal relative to the signal of the excitation light; a cooled, highly sensitive CCD camera with image amplifier is used for detection. Lifetime measurements in a range of a few nanoseconds, e.g. of rhodamine stains, are possible herewith.

Evaluation Example 3:

An epifluorescence illumination apparatus is used in which the emission of a pulsed titanium sapphire laser with pulses in the 100 femtosecond range (see P. Hänninen et al., Appl. Phys. Lett. 66: 1698 (1995)) is used instead of a xenon flash lamp, and a streak camera is used for high-time-resolved detection of the spectral fluorescence emission. It is also possible therewith to use fluorochromes with lifetime half-life times in the nanosecond range, e.g. rhodamine derivatives.

Evaluation Example 4:

A confocal laser scanning fluorescence microscope (see C. Cremer and T. Cremer, Microsc. Acta 81: 31 (1978); G. Brakenhoff et al., Nature 317: 748 (1985): R. W. Wijnaendts van Resandt et al., J. Microsc. 138: 29 (1985)) is used for registering and recording the fluorescence emission of the nucleic acid sequence of the invention. The scanning speed, repetition rate, lenses of the detection ray path as well as the light detection elements and their noise behavior are adapted in such a manner thereby that a sufficient fluorescence quantum statistics is realized at a sufficient signal/noise :ratio. If one starts from an effective confocal detection volume of 0.02 $\mu m^3$, the fluorescence emission of a total of approximately $3 \times 10^5$ base pairs is detected if a traditional chromosome preparation is used. Since a DNA section with a label "1" can be measured in the presence of a 1000-fold excess of DNA sections of a label "2" with the confocal detection method even when using fluorochromes of the same fluorescence lifetime but different spectral fluorescence emission, a nucleic acid sequence in accordance with the invention can be detected. In as far as a start is made from such a ratio in the present example a 300 bp-long DNA section with a label "1" can still be detected.

Evaluation Example 5:

An optical fluorescence near-field microscope is used for fluorescence detection (see E. Betzig et al., Bioimaging 1: 129 (1993); E. Monson et al., Ultramicroscopy 57: 257 (1995); G. Tarrach et al., Rev. Sci. Instr. 66: 3569 (1995)). In a preferred embodiment of fluorescence near-field microscopy the object is illuminated with the aid of a fine tip aperture for concentrating the exciting laser light point for point. The fluorescence emission is collected by a microscope lens with a high numerical aperture and registered with highly light-sensitive sensors.

The effective detection volume can be limited to approximately 0.0003 to 0.00003 $\mu m^3$ by fluorescence nearfield microscopy. Then, given a DNA density of 16 million base pairs per $\mu m^3$ as assumed above, approximately 5,000 to 500 base pairs are registered. If the nucleic acid sequence of the invention is in the detection volume, the excess of the non-informative DNA molecules at a detection volume of 0.0003 $\mu m^3$ is at the most a factor of approximately ten times. At the smaller detection volume of 0.00003 $\mu m^3$ practically only the nucleic acid sequence of the invention is still contributing to the detected fluorescence emission. In both instances an especially high contrast between chromosomal and DNA sites with and without the bonding of a nucleic acid sequence in accordance with the invention results.

If the DNA COMET ASSAY targets are examined instead of chromosomal targets the detection of the nucleic acid sequence of the invention can be simplified if the excess of other labeled DNA sequences is less on account of the lower concentration due to the electrophoretic separation.

Given the presence of one or several translocations between a first and a second chromosome, the site or sites of a sequence of the second fluorescence label down to a few hundred bp long can be demonstrated on the first chromosome, and on the second chromosome the site or sites of a sequence of the first fluorescence label down to a few hundred bp long can be demonstrated. The breaking points can now be optionally isolated, amplified and their correlation with other sequences and their localization on these chromosomes examined in detail.

If a large number of randomly distributed translocation breaking points is present, a fluorescence ratio can be calculated between the first and the second chromosomes of second label/first label and first label/second label which deviates from the other chromosomes. If clusters of translocation breaking points occur, the local distribution of the second label on the first chromosome and the first label on the second chromosome will be different, that is, deviate from a homogeneous mixed staining.

The in situ hybridization of the method of the invention can be carried out with different DNA- or chromosome preparations. For example, in single-cell gel electrophoresis the cells are lysed in situ after the action of DNA-damaging substances and an electrophoresis carried out (see the above-described COMET ASSAY). If there is a fragmentation of DNA of the cells concerned, a type of "comet tail" is produced in the vicinity of the cells concerned. In the past only the distribution of fragments was measured. The use of the method of the invention, especially the in situ hybridization according to step (g) of the method of the invention, can furnish information about how frequently corresponding translocations occur in the fragmented DNA of the "comet tails".

The use of the method of the invention for normal cells of a donor (e.g. from archived material) is also of interest. In the case of known breaking-point regions the traditional fluorescence in situ hybridization on interphase nuclei offers a superior possibility of analysis. However, the method is not economical without knowledge of the exact breaking-point sequences. This disadvantage can be eliminated by the method of the invention, in which in step (g) an in situ hybridization is carried out on normal chromosomes of the donor. The in situ hybridization on cellular DNA of the donor (e.g. from archived biopsy material) after the COMET ASSAY has been carried out can yield information about the variability of the occurrence of translocation events in the tissue examined and thus be prognostically significant.

The method of the invention for demonstrating translocation breaking points on chromosomes can also be carried out with more than two chromosomes, especially when using fluorescence-labeled nucleic acid sequences and evaluation via fluorescence lifetime measurements. For example, in order to produce the nucleic acid sequences in accordance with the invention, aside from DNA probes which are specific for a first chromosome and carry a first label, and DNA probes which are specific for a second chromosome and carry a second label, DNA probes of a third chromosome with a third label, of a fourth chromosome with a fourth label, etc. are taken. For example, five different labels can be distinguished from each other on the basis of their fluorescence emission spectrum. Thus, at least five different labels can be carried out. A translocation is present if a hybridized DNA probe with a first or second or fourth or fifth label is detected on a normal chromosome with a certain label, e.g. a third label, in an in situ hybridization with the nucleic acid sequences produced in an analogous manner as in the case of two labels. Translocation breaking points of five different chromosomes can be demonstrated at the same time therewith.

If labels with differing lifetimes are additionally used it is possible to detect even more translocation breaking points. A first label can take place e.g. with a fluorescence emission F1 and a fluorescence lifetime T1; a second label can take place with F1 and a fluorescence lifetime T2; a third label with F1, T3; a fourth with F1, T4; a fifth with F1, T5; a sixth with a fluorescence emission F1, T1; a sixth with F1, T2; an (n)th with Fn, Tn. Translocation breaking points between material from e.g. a 9th and a 22nd chromosome are accordingly detected in a hybridization in accordance with the invention on normal chromosomal preparations in that a hybridized DNA probe with a 22nd label is discovered on a normal chromosome with a 9th label, as well as a hybridized DNA probe with a 9th label being demonstrated on a normal chromosome with a 22nd label.

Thus, the method of the invention can be modified in such a manner that translocation breaking points from e.g. all 24 human chromosome types can be detected simultaneously.

FIGS. 1A–1G are a schematic presentation of a preferred embodiment of the method of the invention for demonstrating translocation breaking points on chromosomes.

In order to make possible the greatest possible clarity of the schematic presentation the sketched presentation is limited in the following to DNA molecules stemming from a first, normal chromosome (chr A) and a second, normal chromosome (chr B). The expansion of the method to further chromosomes was explained in detail above.

FIG. 1A shows genomic, double-stranded DNA molecules of a donor after isolation and optional amplification. Double-stranded DNA molecules which do not stem from chr A or chr B are designated as "other" DNA molecules; cf. step (a) of the method of the invention.

FIG. 1B shows double-stranded DNA-fragments of donor DNA after fragmentation on e.g. 1–2 kbp-long fragments, e.g. with the aid of restriction endonucleases.

The solution contains: DNA fragments (A) from donor DNA which correspond in their base sequence to sequences of a first, normal chromosome (chr A); DNA fragments (B) from donor DNA corresponding in their base sequence to sequences of a second, normal chromosome (chr B); DNA fragments (AB) from donor DNA in which there is a fusion or translocation of sequences from chr A and chr B; these latter pieces represent the donor DNA at a translocation breaking point between DNA of a first chromosome chr A and DNA of a second chromosome chr B; other DNA fragments stemming neither from chr A nor from chr B; cf. step (b) of the method of the invention.

FIG. 1C shows the DNA fragments of the donor DNA of FIG. 1B after denaturation. The following are found as result in the solution: Single-stranded DNA molecules (A*) from the denaturation of double-stranded DNA fragments (A); single-stranded DNA molecules (B*) from the denaturation of double-stranded DNA-fragments (B); single-stranded DNA molecules (A*B*) from the denaturation of double-stranded DNA fragments (AB); single-stranded DNA molecules with "other" sequences of donor DNA; cf. step (c) of the method of the invention.

FIG. 1D shows the hybridization using the denatured DNA fragments shown in FIG. 1C, also called single strands, as matrix, as well as shows DNA probes which stem from a first, normal chromosome (chr A) and carry a first label F1 (A), as well as DNA probes which stem from a second, normal chromosome (chr B) and carry a second label F1 (B). The DNA probes from chr A hybridize on denatured DNA fragments (A*) as well as on the section of the denatured DNA fragments (A*B*) complementary to them; the DNA probes of chr B hybridize to denatured DNA fragments (B*) as well as to the section of denatured DNA fragments (A*B*) complementary to them. Under suitable reaction conditions the solution also contains "other" DNA molecules which are usually present as double strands after the end of the reaction and which carry neither a fluorescence label F1(A) nor a fluorescence label F1(B); cf. step (d) of the method of the invention.

FIG. 1E shows the synthesis of the nucleic acid sequence of the invention using the DNA probes from chr A and chr B hybridized to the individual strands (A*B)*); cf. step (e) of the method of the invention.

FIG. 1F shows the isolation of the nucleic acid sequence of the invention. Isolation method I, which is based on a simple denaturation, is shown as example. In particular, the single-stranded nucleic acid sequence of the invention with first fluorescence labels F1 (A) and second fluorescence labels F1(B) are located in the solution after execution of the denaturation step; the nucleic acid sequence has a base sequence complementary to the individual strand (A*B) functioning as matrix. In addition thereto, the following are also present in the solution in isolation method I: DNA molecules labeled with F1(A) and with a base sequence complementary to (A*); DNA molecules labeled with F1(B) and with a base sequence complementary to (B*); as well as other, nonlabeled, single-stranded sequences of other chromosomes than chr A or chr B. Sequences of other chromosomes with a base sequence also occurring on chr A or chr B can likewise be labeled with F1(A) or F1(B). This concerns in particular repetitive sequences (R); cf. step (f) of the method of the invention.

FIG. 1G shows the result of the evaluation of the in situ hybridization, carried out according to step (g), of the nucleic acid sequence obtained after isolation method I or II on normal, first chromosomes chr A and second, normal chromosomes chr B.

In an embodiment of the invention the translocation breaking points can be recognized by the occurrence of second labels F1(B) on first chromosomes chr A and of first labels F1(A) on second chromosomes chr B. The other chromosomes, to the extent present in the preparation, carry no first or second label when the in situ hybridization is carried out in accordance with the invention. In particular, when a nucleic acid sequence after isolation method I is used the suppression of repetitive sequences is advantageous; cf. step (h) of the method of the invention.

I claim:

1. A method of producing a nucleic acid sequence specific for a translocation breaking point on a chromosome, said method comprising the steps:
    (a) cleaving genomic DNA comprising at least one translocation breaking point between two chromosomes into DNA fragments,
    (b) denaturing said DNA fragments into single strands,
    (c) hybridizing said single strands in solution in a reaction mixture with a first batch of DNA probes which comprise a first label and are specific for a first chromosome, and with a second batch of DNA probes which comprise a second label and are specific for a second chromosome,
    (d) synthesizing said nucleic acid sequence using said single strands as a template in the presence of nucleotides and at least one agent suitable for synthesizing nucleic acids and one agent suitable for linking nucleic acids, and
    (e) isolating said nucleic acid from said reaction mixture, in which a first sequence section of the isolated nucleic acid sequence comprises a DNA probe from said first batch and a second sequence section of the isolated nucleic acid sequence comprises a DNA probe from said second batch.

2. The method according to claim 1 in which the agent suitable for synthesizing nucleic acids is selected from the group consisting of a taq polymerase, a Klenow fragment of DNA polymerase I, an *E. coli* DNA polymerase I, and a reverse transcriptase.

3. The method according to claim 1 in which the agent suitable for linking nucleic acids is selected from the group consisting of T4 ligase, *E. coli* ligase, and a linking polymerase.

4. The method according to claim 1 in which the first and the second labels are different fluorescent stains.

5. A method for demonstrating translocations between chromosomes and translocation breaking points on chromosomes, comprising the steps:
    (a) isolating genomic DNA to be examined from suitable cellular material of a donor,
    (b) cleaving said genomic DNA into double-stranded DNA fragments,
    (c) denaturing said double-stranded DNA fragments into a first set of single strands,
    (d) hybridizing said first set of single strands in a reaction mixture with a first batch of DNA probes which have a first label and are specific for a first chromosome and with a second batch of DNA probes which have a second label and are specific for a second chromosome,
    (e) synthesizing of nucleic acids using said first set of single strands as a template in the presence of nucleotides and at least one agent suitable for the synthesis of nucleic acids and of an agent suitable for linking nucleic acids, producing reaction products present in double strands,
    (f) denaturing said reaction products present in double strands into a second set of single strands, yielding single-stranded nucleic acids with said first label, single-stranded nucleic acids with said second label and, given the presence of a translocation between said first chromosome and said second chromosome of said donor, nucleic acid sequences specific for a translocation breaking point in said reaction mixture,
    (g) hybridizing said second set of single-stranded nucleic acid sequences in situ with a first and a second control chromosome without translocations or with DNA separated by single-cell gel electrophoresis and
    (h) evaluating said in situ hybridization via the different labels of the nucleic acid sequences of step (f).

6. The method according to claim 5, in which the agent suitable for synthesizing nucleic acids is selected from the group consisting of a taq polymerase, a Klenow fragment of DNA polymerase I, an *E. coli* DNA polymerase I, and a reverse transcriptase.

7. The method according to claim 5 in which the agent suitable for linking nucleic acids is selected from the group consisting of T4-DNA ligase, *E. coli* ligase and a linking polymerase.

8. The method according to one of claims 5 to 7 in which the first and the second labels are different fluorescent stains.

9. The method according to claim 5 in which the donor is a human.

10. The method according to claim 5 in which the donor is not human and belongs to the group of mammalia.

11. The method according to claim 5 wherein said isolation step further comprises isolating DNA from a malignancy.

* * * * *